US008998885B2

(12) United States Patent
Nelson et al.

(10) Patent No.: US 8,998,885 B2
(45) Date of Patent: Apr. 7, 2015

(54) SYSTEM AND METHOD FOR INTRAPARENCHYMAL DRUG INFUSION

(75) Inventors: Brian D. Nelson, Birchwood, MN (US); Ann M. Gronda, New Brighton, MN (US); Matthew H. Adams, Zimmerman, MN (US)

(73) Assignee: Medtronic, Inc., Minneapolis, MN (US)

( * ) Notice: Subject to any disclaimer, the term of this patent is extended or adjusted under 35 U.S.C. 154(b) by 1183 days.

(21) Appl. No.: 12/881,732

(22) Filed: Sep. 14, 2010

(65) Prior Publication Data
US 2011/0004159 A1 Jan. 6, 2011

Related U.S. Application Data

(62) Division of application No. 11/552,400, filed on Oct. 24, 2006, now Pat. No. 7,794,443.

(51) Int. Cl.
| A61K 9/22 | (2006.01) |
| A61M 5/145 | (2006.01) |
| A61M 5/142 | (2006.01) |
| A61M 5/168 | (2006.01) |

(52) U.S. Cl.
CPC ......... *A61M 5/1452* (2013.01); *A61M 5/14276* (2013.01); *A61M 5/16854* (2013.01); *A61M 2205/3331* (2013.01); *A61M 2205/52* (2013.01); *A61M 2210/0693* (2013.01)

(58) Field of Classification Search
CPC ............... A61M 5/14276; A61M 5/16854; A61M 2205/3331; A61M 2205/52; A61M 2210/0693
USPC ............... 604/67, 65, 890.1, 891.1, 505, 503
See application file for complete search history.

(56) References Cited

U.S. PATENT DOCUMENTS

| 5,087,245 A * | 2/1992 | Doan ............................. 604/67 |
| 5,720,720 A | 2/1998 | Laske et al. |
| 6,272,370 B1 | 8/2001 | Gillies et al. |
| 6,549,803 B1 | 4/2003 | Raghavan et al. |
| 7,320,676 B2 | 1/2008 | Miesel |

(Continued)

FOREIGN PATENT DOCUMENTS

| EP | 0 248 633 A2 | 9/1987 |
| EP | 0 361 793 A2 | 4/1990 |

(Continued)

OTHER PUBLICATIONS

PCT Search Report (for PCT Application No. PCT/US2007/082357) dated Oct. 24, 2007; 7 pgs.

*Primary Examiner* — Kevin C Sirmons
*Assistant Examiner* — Deanna K Hall
(74) *Attorney, Agent, or Firm* — Dicke, Billig & Czaja, PLLC

(57) ABSTRACT

A system for performing an intraparenchymal drug infusion including a pump device, a delivery tube, a sensor, and a processor. The tube is fluidly coupled to the pump device, establishing an infusate pathway from the pump to an infusate exit port of the delivery tube. The sensor is positioned to sense a parameter indicative of pressure in the infusate pathway. Finally, the processor is programmed to generate information indicative of infusate delivery effectiveness of a drug infusion procedure based upon information from the sensor. In some embodiments, the processor generates a net infusion pressure profile, such as a pressure-time curve, and prompts display of the pressure profile to a neurosurgeon for subsequent evaluation of infusate delivery effectiveness.

22 Claims, 15 Drawing Sheets

(56) References Cited

U.S. PATENT DOCUMENTS

| | | |
|---|---|---|
| 2001/0027599 A1 | 10/2001 | Elsberry |
| 2005/0075624 A1 | 4/2005 | Miesel |
| 2006/0089544 A1 | 4/2006 | Williams, Jr. et al. |
| 2007/0016046 A1* | 1/2007 | Mozayeni et al. ............ 600/443 |
| 2007/0270782 A1 | 11/2007 | Miesel et al. |

FOREIGN PATENT DOCUMENTS

| | | |
|---|---|---|
| EP | 1 529 546 A1 | 5/2005 |
| WO | 2005/105182 A1 | 11/2005 |
| WO | 2007/123764 A2 | 11/2007 |

* cited by examiner

SYSTEM AND METHOD FOR INTRAPARENCHYMAL DRUG INFUSION

CROSS-REFERENCE TO RELATED APPLICATIONS

This application is a divisional of U.S. patent application Ser. No. 11/552,400, filed Oct. 24, 2006, entitled "System and Method for Intraparenchymal Drug Infusion"; and the entire teachings of which are incorporated herein by reference.

BACKGROUND

The present disclosure relates to intraparenchymal drug infusion, for example by means of convection enhanced delivery (CED). More particularly, it relates to systems and methods for evaluating infusate delivery effectiveness as part of an intraparenchymal drug infusion procedure.

Intraparenchymal (IPA) drug infusion is useful in effectuating a variety of medical treatments at a target tissue site of various anatomical areas. For example, intracerebral IPA drug infusion is a common technique for delivering drugs to selected portions of a patient's brain, relying upon convection to directly infuse brain tissue with therapeutic drugs thereby bypassing the blood-brain barrier. In general terms, IPA drug infusion can be performed on an acute or chronic basis, and typically entails an exit port of a delivery tube (e.g., catheter) being positioned at the tissue target site. The drug (e.g., pharmaceutically active agent that can include biologic materials such as protein(s), virus(es), RNA strands, etc.) is provided in a liquid format (e.g., mixed with saline) and is forced through the delivery tube and thus to the target site, for example via an infusion pump that can be located external the patient or implanted (along with the delivery tube) within the patient.

Effective IPA drug therapy requires successful delivery of the drug. A selected drug likely cannot provide desired therapeutic results without reaching, and subsequently being generally retained at, the intended target site or region. For many IPA drug infusion procedures, it is exceedingly difficult to determine whether or not the drug was successfully or accurately delivered, due to the highly confined nature of the organ/parenchymal tissue in question (e.g., a neurosurgeon cannot readily visualize the brain parenchyma/infusate interface in connection with an intracerebral IPA drug infusion procedure as the exit port of the delivery tube is buried within the brain). Under these circumstances, an available technique for confirming delivery effectiveness is to include a surrogate tracer in the infusate and monitor the volume of distribution in real-time using intraoperative imaging (e.g., MRI). Unfortunately, FDA-approved surrogate tracers are not available for many therapeutic agents. Further, operating rooms typically do not include an MRI system (or similar imaging system). As a result, conventional IPA drug infusion procedures do not afford the neurosurgeon with images of the delivered infused media, such that for many IPA procedures, the neurosurgeon has no positive feedback regarding infusate delivery effectiveness, and thus cannot evaluate whether targeted tissue was infused and/or that it was infused to a desired extent.

In light of the above, a need exists for IPA drug infusion systems and methods that provide feedback to the neurosurgeon or other user from which an evaluation as to infusate delivery effectiveness of the infusion procedure can be performed.

SUMMARY

Some aspects in accordance with principles of the present disclosure relate to a system for performing an intraparenchymal drug infusion. The system includes a pump device, a delivery tube terminating at an infusate exit port, a sensor, and a processor. The delivery tube is fluidly coupled to the pump device, establishing an infusate pathway from the pump to the infusate exit port of the delivery tube. The sensor is positioned to sense a parameter indicative of pressure in the infusate pathway, and can be in direct or indirect fluid communication with the infusate pathway. Finally, the processor is programmed to generate information indicative of infusate delivery effectiveness of a drug infusion procedure based upon information from the sensor. In some embodiments, the processor generates a pressure profile, such as a net infusion pressure-time curve, and prompts display of the pressure profile to a neurosurgeon or other user for evaluation of infusate delivery effectiveness.

Other aspects relate to a method of performing an intraparenchymal drug infusion procedure, and includes positioning an infusate exit port of a delivery tube at an intraparenchymal target site. The target site is infused with drug by pumping the drug through an infusate pathway formed by the tube. Information indicative of a pressure of the infusate pathway is monitored during infusion of the target site. Finally, infusate delivery effectiveness is evaluated based upon the monitored pressure. In some embodiments, a pressure profile is generated, displayed, and reviewed in evaluating infusate delivery effectiveness.

DETAILED DESCRIPTION

Figure 1:
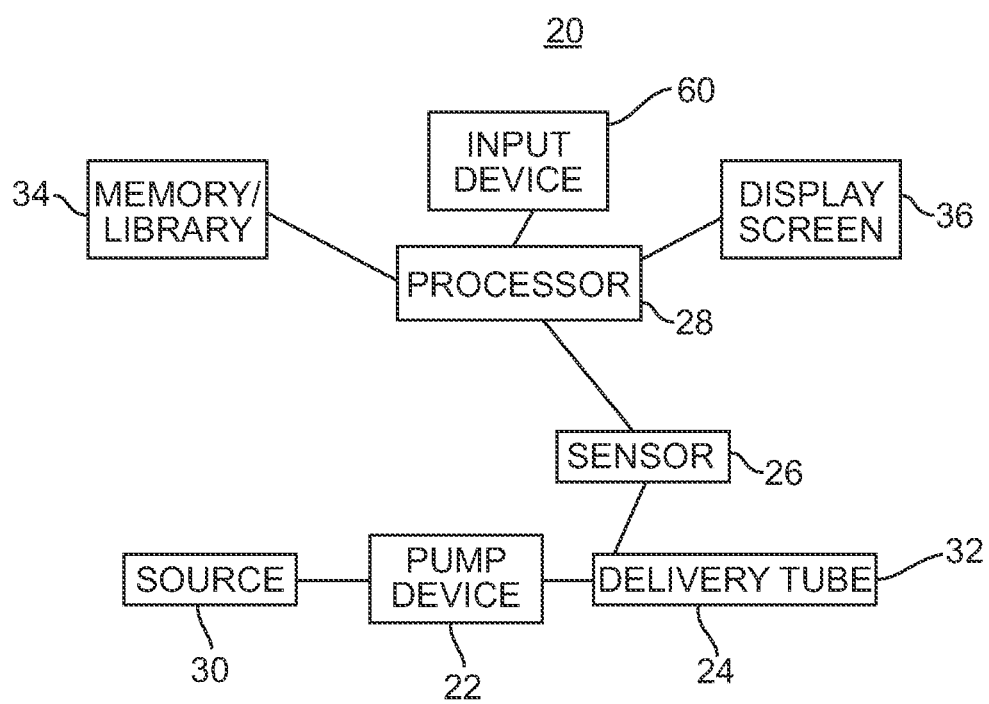
FIG. 1 is a block diagram of an IPA drug infusion system.

One embodiment IPA drug infusion system 20 in accordance with principles of the present disclosure is shown in block form in FIG. 1. The system 20 includes a pump device 22, a delivery tube 24, a sensor 26, and a processor 28. Details on the various components are provided below. In general terms, however, the pump device 22 is fluidly connected to the delivery tube 24, and is adapted to delivery (e.g., at a constant flow rate) a therapeutic drug (not shown) from a source 30 to an infusate exit port(s) 32 of the delivery tube 24 that is otherwise located at a desired target site (e.g., a parenchymal target). In this regard, the pump device 22 and the delivery tube 24 combine to define an infusate fluid flow pathway (or "infusate pathway") from the source 30 to the infusate exit port 32. With this in mind, the sensor 26 is associated with one or both of the pump device 22 and/or delivery tube 24, and is adapted to sense a parameter indicative of a pressure within the infusate pathway. The processor 28 is communicatively connected to the sensor 26, and is adapted or programmed to act upon pressure-related information signaled from the sensor 26. More particularly, and as described in greater detail below, the processor 28 is adapted or programmed to generate information indicative of infusate delivery effectiveness of a current IPA drug infusion procedure performed by, or being performed by, the system 20 based upon the pressure-related information, where "infusate delivery effectiveness" is in reference to the infusate being delivered to, and a therapeutically effective volume of distribution remaining at, the intended target site. Regardless, the so-generated feedback information is then provided to a neurosurgeon or other user, for example via a display screen 36 electronically connected to the processor 28. The user can then evaluate infusate delivery accuracy upon reviewing the feedback information and, where desired, effectuate surgical corrections implicated by the feedback information (e.g., repositioning of the delivery tube 24).

Various ones of the components 22, 24, 26, 28 associated with the system 20 can assume a wide variety of forms appropriate for a particular end-use application. For example, the system 20 can be configured for use in performing an IPA drug infusion procedure on an acute basis (e.g., the pump device 22 is external the patient) or a chronic basis (e.g., the pump device 22 is implanted within the patient). To this end, the pump device 22 is optionally capable of providing a constant infusate flow rate and can be or includes a syringe pump (e.g., programmable syringe pump), peristaltic pump, piston pump, diaphragm pump, osmotic pump, implantable infusion pump (IIP), etc. In other embodiments, the system 20 can include two or more pump devices 22 (and a corresponding number of delivery tubes 24 and sensors 26).

The delivery tube 24 can also assume any form conventionally employed for drug infusions procedures (e.g., tubing, catheter, needle, etc.). As described in greater detail below, in some embodiments, the delivery tube 24 can incorporate one or more features that interface with and/or facilitate use of the sensor 26 (or structures establishing a fluid connection to the sensor 26).

As a point of reference, the system 20 has been described as including pump device 22 and the delivery tube 24. In other embodiments, however, the system in accordance with principles of the present disclosure is used with (e.g., retro-fitted) an existing, separately provided infusion device that otherwise includes a pump device and a delivery tube. Thus, a system in accordance with principles of the present disclosure can consist only of the sensor 26 and the processor 28 as described below, such that the pump device 22 and/or the delivery tube 24 are not required elements.

The sensor 26 can be any known sensor capable of sensing information relating to a desired parameter, such as pressure; for example, the sensor 26 can be a pressure sensor such as pressure transducer. As described in greater detail below, the sensor 26 can be fluidly connected in-line to or with the delivery tube 24 (and in particular the infusate pathway) for directly sensing a fluid pressure within the delivery tube 24, or can be fluidly connected to an auxiliary pathway (not shown) terminating at or adjacent the infusate exit port 32 for sensing pressure in tissue surrounding the infusate exit port 32. With this second approach, the sensed pressure represents a close approximation of pressure within the delivery tube 24/infusate pathway.

Finally, the processor 28 can be a computing device that includes a microprocessor as known in the art, and can further include or be provided as part of a controller or data acquisition unit that also provides or is connected to a memory 34 and the display screen 36.

The system 20 can be adapted to effectuate an IPA drug infusion procedure at virtually any parenchymal tissue/organ, with the delivered infusate being any therapeutic composition current known or in the future developed. For purposes of illustration, the following discussion is in the context of an intracerebral target site (e.g., brain parenchyma), it being understood that this one exemplary application is in no way limiting.

In some embodiments, operation of the system 20 to generate information indicative of infusate delivery effectiveness is premised upon the processor 28 utilizing information from the sensor 26 to formulate or create a pressure profile (e.g., a pressure-time curve) for the infusion procedure, with this pressure profile conveying information relating to one or more characteristics of effective infusate delivery, either alone or based upon a comparison with a template or reference pressure profile. As a point of reference, IPA drug infusion entails the infused therapeutic drug mixing and displacing interstitial fluid otherwise occupying the extracellular space surrounding the cells at the infusion target site. Once in the extracellular space, the target cells (e.g., diseased cells) are free to uptake the delivered drug. As more drug is pumped into the tissue, the volume of distribution expands until a steady state drug delivery condition occurs where the infusion rate equals the rate of clearance. Clearance is achieved through cellular uptake, drug metabolism, and interstitial fluid flow clearance. It has surprisingly been found that at steady state drug delivery, the volume of distribution stops expanding and remains constant. Throughout this volume of distribution, the drug concentration gradient varies with the highest concentration at the delivery tube entry point (i.e., the infusate exit port 32) and the lowest concentration at the outer surface of the volume distribution. The effective concentration (i.e., the lowest concentration where the drug still has therapeutic effect) forms the outer boundary of the effective volume of distribution, which is a subset of the overall volume of distribution.

Figure 2:
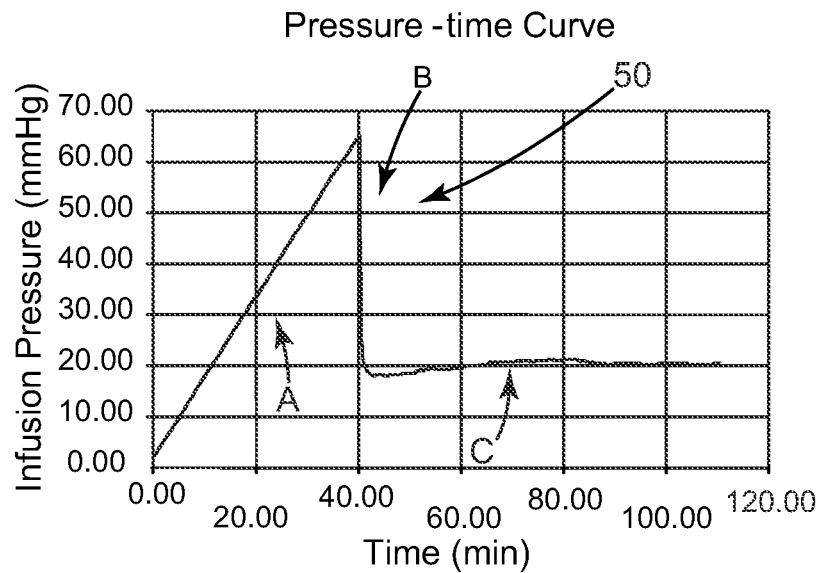
FIG. 2 is an exemplary pressure profile generated by the system of FIG. 1.

With the above in mind, it has surprisingly been found through experimentation that successful (i.e., accurate or effective infusate delivery) constant flow rate IPA drug infusions have identifiable pressure profile characteristics for at least some parenchymal infusion sites (e.g., intracerebral). In particular, FIG. 2 illustrates representative a pressure-time curve 50 for an effective IPA drug infusion (it being noted that the pressure-time curve 50 was formulated in connection with a constant flow rate IPA drug infusion experimentally performed on ovine brain tissue and visually confirmed to have had an accurate or effective infusate delivery). It has been discovered that the pressure-time curve 50 can be demarcated into three regions: an initial region A characterized by a sharp rise in pressure; an intermediate region B characterized by a sharp decline in pressure forming a saw tooth shape; followed by a flat, relatively constant pressure region C that continues indefinitely. The constant pressure region C can be referred to as the steady state pressure, and has surprisingly been found to consistently form before the steady state drug delivery condition described above is achieved.

With additional reference to FIG. 1, the IPA drug infusion system 20 incorporates the above discoveries in presenting the user with predictive information relating to infusate delivery effectiveness of an IPA drug delivery procedure via a formulated pressure profile. In some embodiments, the processor 28 operates to formulate the pressure profile (e.g., as a pressure-time curve) based on information from the sensor 26, and then prompts the display of the pressure-time curve (and/or other information) to the user for evaluation. The pressure profile generated by the processor 28 can assume a variety of other forms a differing from a pressure-time curve and still convey information useful in evaluating one or more aspects relating to infusate delivery effectiveness. For example, the pressure profile can be a time-pressure curve, a collection of pressure values in a non-graphical form, average pressure(s), area under the pressure-time curve, a parameter or series of parameters describing the pressure-time curve, etc. Thus, the phrase "pressure profile" as used throughout this specification is not limited to a pressure-time curve.

Figure 3A:
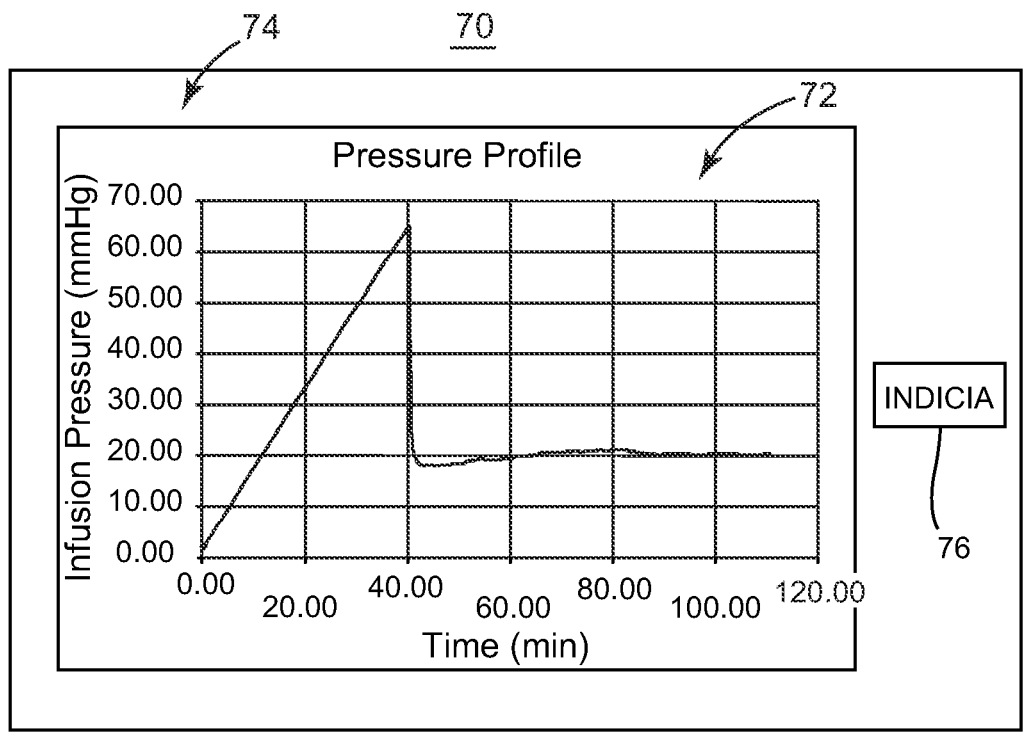
FIGS. 3A-3C are exemplary displays generated by the system of FIG. 1.

The formulated pressure profile can be presented to a user for subsequent evaluation via the display 36. In some embodiments, the pressure profile can be formulated and presented to the user in terms of the infusate pathway pressure (e.g., fluid pressure within the delivery tube 24) as measured by the sensor 26. FIG. 3A provides an exemplary display 70 in accordance with this but one embodiment, and reflects one possible presentation of a pressure profile 72 on a display screen 74 (that can otherwise assume any conventional form), with the pressure profile 72 being formulated as the fluid pressure measured by the sensor 26.

Alternatively, or in addition, the processor 28 (FIG. 1) can be adapted or programmed to account for a baseline pressure of the target site (and variations thereof) in formulating the pressure profile as presented to the user, and/or can prompt the display of baseline pressure information in conjunction with the displayed measured pressure profile, and/or can formulated a net infusion pressure based upon the measured pressure and the baseline pressure, with this net infusion pressure serving as the basis for the pressure profile presented to the user (alone or in conjunction with one or both of a pressure profile of the measured pressure and/or a pressure profile of the baseline pressure). As a point of reference, the baseline pressure is the sum of the interstitial fluid pressure (i.e., pressure of the target site at the infusate exit port 32 (FIG. 1)) and the hydrostatic pressure difference between the height of the pressure sensor 26 (FIG. 1) and the infusate exit port 32. For example, with intracerebral infusion, cranial pressure of the patient can be used as a measure of the interstitial fluid pressure. The net infusion pressure, in turn, is the measured pressure (as measured at the sensor 26) minus the baseline pressure. Effectively, then, the net infusion pressure is the pressure required to infuse the drug through the tissue at the target site.

Figure 3B:
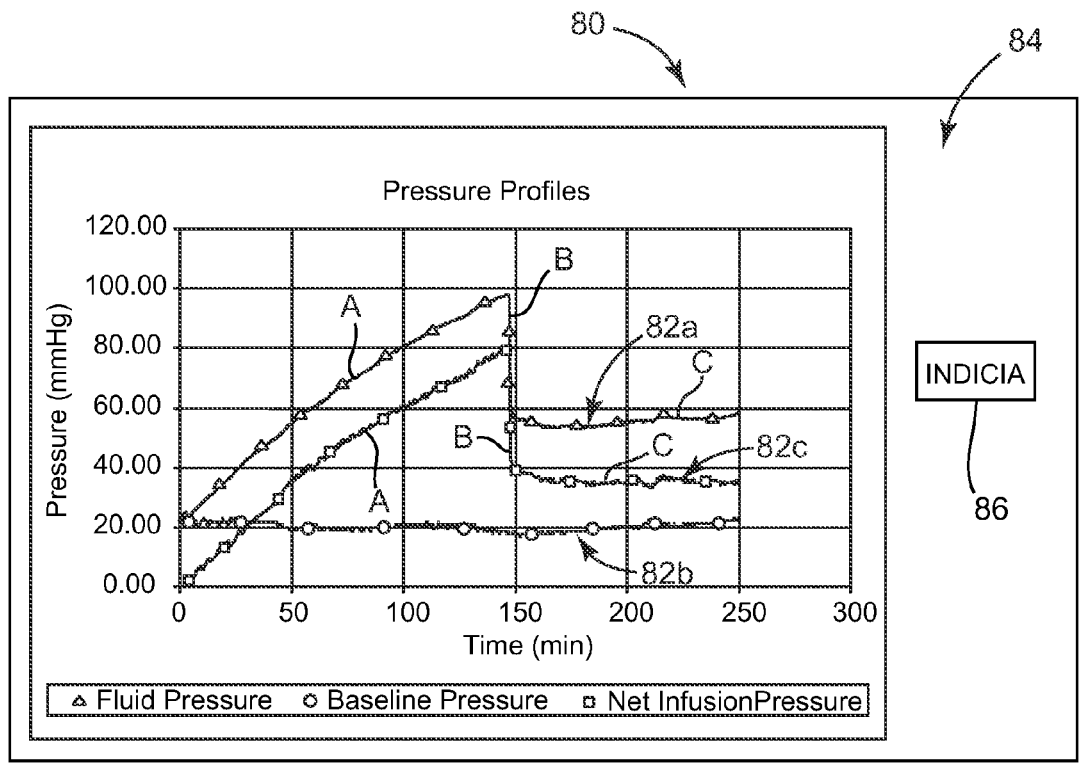

With the above in mind, FIG. 3B provides an exemplary display 80 generated by the system 20 in accordance with some embodiments. In particular, first, second, and third pressure profiles 82a-82c are displayed on a display screen 84 in connection with an IPA infusion procedure performed by, or being performed by, the system 20 (FIG. 1). The first pressure profile 82a is based upon fluid pressure as measured by the sensor 26 (FIG. 1), the second pressure profile 82b is based upon baseline pressure as determined by the processor 28 (FIG. 1), and the third pressure profile 82c is based upon net infusion pressure as determined by the processor 28. In some embodiments, the system 20 is configured such that the baseline pressure is constantly and independently measured throughout the entire infusion monitoring period, for example using a separate tube (e.g., a Millar catheter) that provides a constant indication of actual target site pressure. This constant measure of baseline pressure is reflected in the baseline pressure profile 82b of FIG. 3B). Alternatively, an initial baseline pressure can be established prior to infusate delivery (e.g., the infusate pathway of the inserted delivery tube 24 is primed (filled with infusate) and a pressure at the sensor 26 is measured before the pump device 22 is activated, with this initial baseline pressure being used for determining the net infusion pressure throughout the infusion monitoring period).

While the display 80 includes each of the measured or fluid pressure profile 82a, the baseline pressure profile 82b, and the net infusion pressure profile 82c, in other embodiments only the net infusion pressure profile 82c and the baseline pressure profile 82b are displayed to the user; and in yet other embodiments, only the net infusion pressure profile 82c is displayed. Conversely, the processor 28 (FIG. 1), can be adapted or programmed to prompt the display of additional information, represented generally in FIG. 3B as indicia 86 (it being understood that the display 70 of FIG. 3A can also include similar indicia 76). The indicia 86 can convey a wide variety of different information that assists a user in evaluating the displayed pressure profile(s). For example, with embodiments in which the baseline pressure profile 82b is not displayed, the indicia 86 can reflect a measured baseline pressure (e.g., in numerical form). However, the indicia 86 is not a required feature of the system 20, and thus can be eliminated in other embodiments.

Figure 3C:
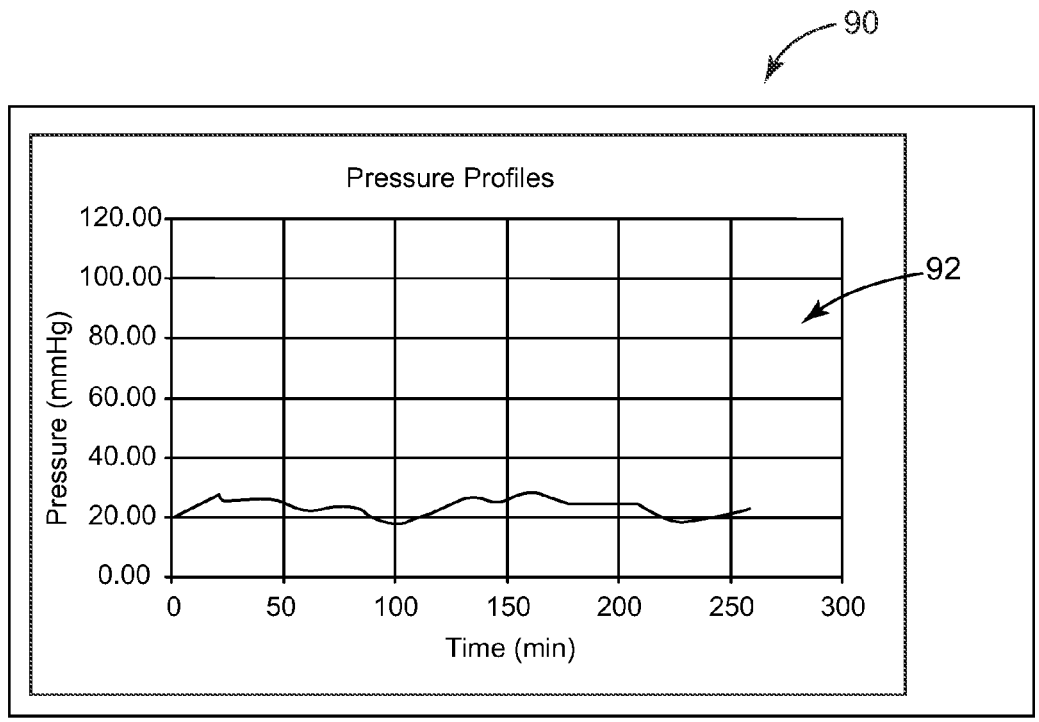

Regardless of exact form, the pressure profile, as formulated and displayed by the system 20 (FIG. 1) provides the user (e.g., neurosurgeon) with information indicative of infusate delivery effectiveness. For example, where the displayed pressure profile (e.g., the measured pressure profile and/or the net infusion pressure profile) does not evidence discernable initial, intermediate and constant pressure regions A, B, C (FIG. 2), the user is alerted to the possibility that the infusion was not successful (in terms of infusion delivery effectiveness). By way of reference, the measured pressure profile 72 of FIG. 3A and the measured and net infusion pressure profiles 82a, 82c of FIG. 3B are indicative of a successful infusion (i.e., effective infusate delivery) in that each profile reflects a discernable initial region A having an increasing pressure, an intermediate region B characterized by a sharp drop in pressure, and a constant pressure region C. By way of comparison, the display 90 of FIG. 3C includes a net infusion pressure profile 92, as formulated by the system 20 (FIG. 1) during an IPA infusion procedure, displayed on a display screen 94. The pressure profile 92 does not reflect expected profile regions in that a peak pressure (region A of FIG. 2) is never formed, and thus is indicative of ineffective infusate delivery. As such, embodiments in accordance with aspects of the present disclosure entail formulation and display of only one of the measured pressure profile or a net infusion pressure profile to provide a user with information indicative of infusate delivery effectiveness.

In other embodiments, the system 20 (FIG. 1) can provide the user with additional information from which further aspects of infusate delivery effectiveness can be evaluated. For example, the net infusion pressure profile can be formulated and displayed along with baseline pressure information (either as a constant, initial value or as a continuously measured/determined pressure profile), with the user then comparing the net infusion pressure profile with the baseline pressure information in evaluating infusate delivery effectiveness. In this regard, where the comparison reveals that the constant pressure region (C in FIG. 2) of the net infusion pressure profile is not higher than the baseline pressure value/profile, it can be concluded that the infusion delivery was unsuccessful. Even further, this same comparison can provide the user with sufficient feedback information to conclude that leakage has occurred or is occurring as described below.

As a point of reference, convective fluid flow will always seek the path of least resistance; for many target site applications, filling the tortuous crevasses of the extracellular spaces in targeted tissue requires much more pressure than simply flowing "out" of the target tissue. For example, it has surprisingly been found that with intracerebral IPA drug infusion, the infusate may undesirably flow out of the targeted tissue and into the cerebral spinal fluid via ventricles, sinuses, fissures, etc. This infusate leakage is problematic and has a major affect on the volume of infusate distribution; namely the volume of distribution can be greatly stunted as its growth would effectively cease once the infusate finds an alternate path out of the targeted tissue.

Another form of leakage occurs due to backflow. By way of background and with reference to FIG. 1, for many IPA drug infusion procedures, positioning of the infusate exit port 32 of the delivery tube 24 at the parenchymal target site creates a "track" or passage in the tissue within which the delivery tube 24 resides. Depending upon the type of tissue involved and/or the positioning technique, a cross-dimensional size of this tissue passage can be greater than an outer diameter of the delivery tube 24, thereby creating a channel (between the tissue and the delivery tube 24) through which the infusate can undesirably flow. This phenomena is commonly referred to as "backflow" or "back tracking," and is more prevalent with higher infusate flow rates and/or larger diameter delivery tubes, as well with delivery tube insertion techniques in which a larger, more rigid tube (e.g., a cannula) is initially employed to direct the delivery tube 24 to the target site, and then removed or retracted prior to infusion. When backflow occurs, the effect is similar to infusate leakage as described above. Since the infusate flows or tracks "back" up the wall of the delivery tube 24, the volume of distribution forms a narrow, cylindrical shape. For acute applications in which a visible infusate (e.g., dyed or phosphor tagged infusate) is employed, backflow can be visually perceived in the form infusate leaking out of the tissue entry point of the delivery tube 24. Under multiple other circumstances, however, it is highly difficult for a clinician to visually confirm occurrences (or absence) of infusate backflow.

In light of the above, embodiments of the system 20 provide the user with information indicative of infusate leakage. For example, the processor 28 is adapted to formulate a pressure profile (e.g., a net infusion pressure profile) and baseline pressure information for the current IPA drug infusion procedure as described above, and prompt display of the pressure profile and baseline pressure information to the user for subsequent evaluation in determining whether infusate leakage has occurred. By examining or comparing the net infusion pressure profile with the baseline pressure information, infusate leakage can be evaluated. For example, the display 80 of FIG. 3B reflects that the net infusion pressure profile 82c, and in particular the constant pressure region C thereof, does not approach the baseline pressure profile 82b, such that a user can conclude that leakage has not occurred.

Figure 4A:
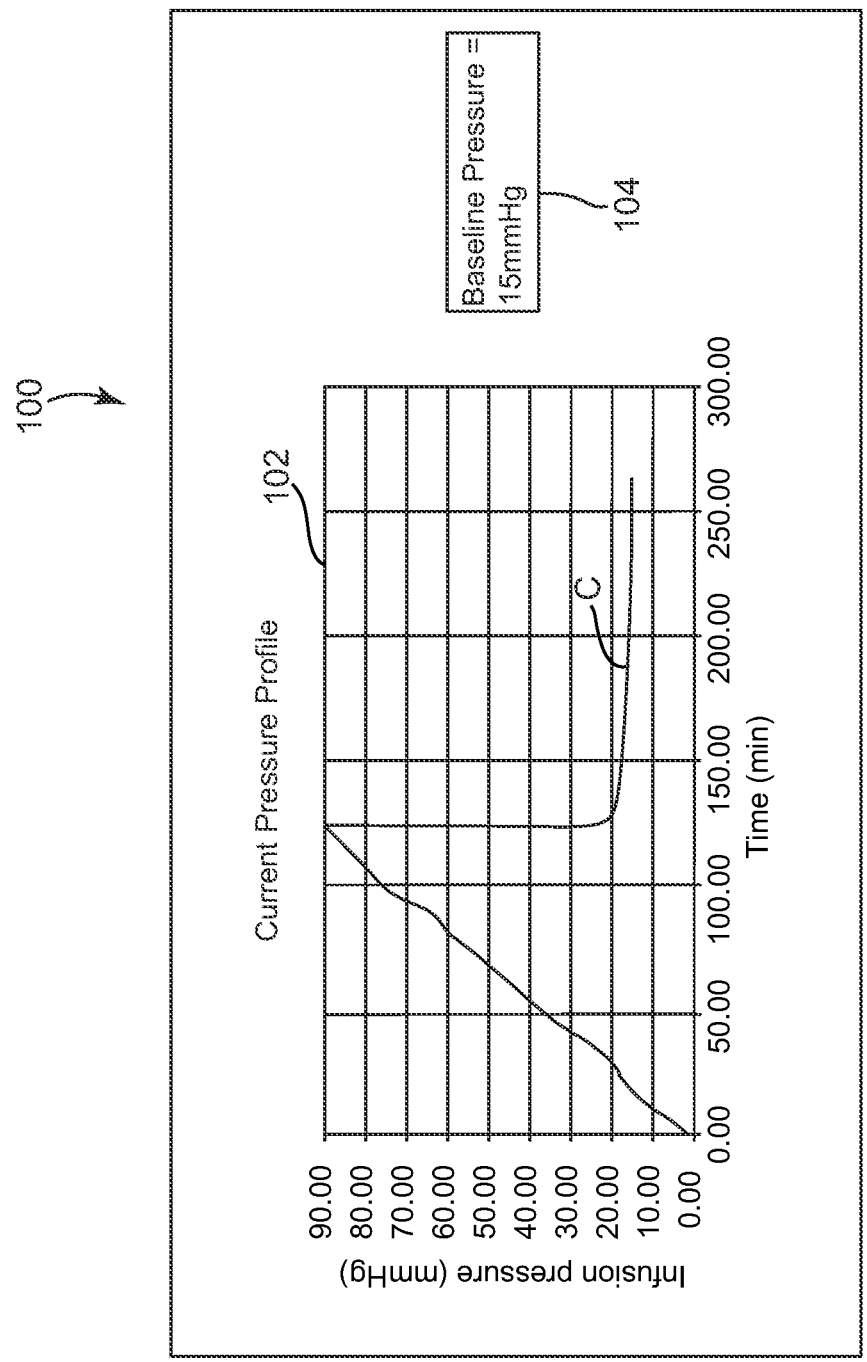
FIGS. 4A-4D are exemplary displays generated by the system of FIG. 1, including exemplary pressure profiles indicative of infusate leakage.

Conversely, FIG. 4A illustrates a display 100 including a formulated pressure profile 102 (e.g., net infusion pressure profile), along with indicia 104 indicative of a baseline pressure associated with the target tissue. The baseline indicia 104 can be in alphanumeric form, shown as a line against the pressure profile 102, etc. Regardless, by comparing the steady state pressure region C of the pressure profile 102 with the baseline indicia 104, a determination can be made as to whether infusate leakage has occurred. With the one example of FIG. 4A, the pressure profile 102 exhibits a steady state pressure approaching 15 mmHg; further, the baseline indicia 104 reflects a baseline pressure of 15 mmHg. Under these conditions, it can be determined that infusate leakage has occurred, as the steady state pressure is approximating or approaching the baseline pressure.

As a point of reference, the pressure profile 102 of FIG. 4A was generated during IPA drug infusion experiments performed on an ovine brain in which infusate leakage was visually confirmed, and a baseline cranial pressure of 15 mmHg was observed. Thus, the ability of the system 20 to provide information indicative of infusate leakage has been confirmed. In other, related embodiments, the display 100 can include further indicia providing instructions to a clinician for analyzing the pressure profile 102; a report or analysis of infusate leakage independently generated by the processor 28 (FIG. 1) in automatically comparing the steady state pressure with the baseline pressure; one or more reference pressure profiles; etc.

Figure 4B:
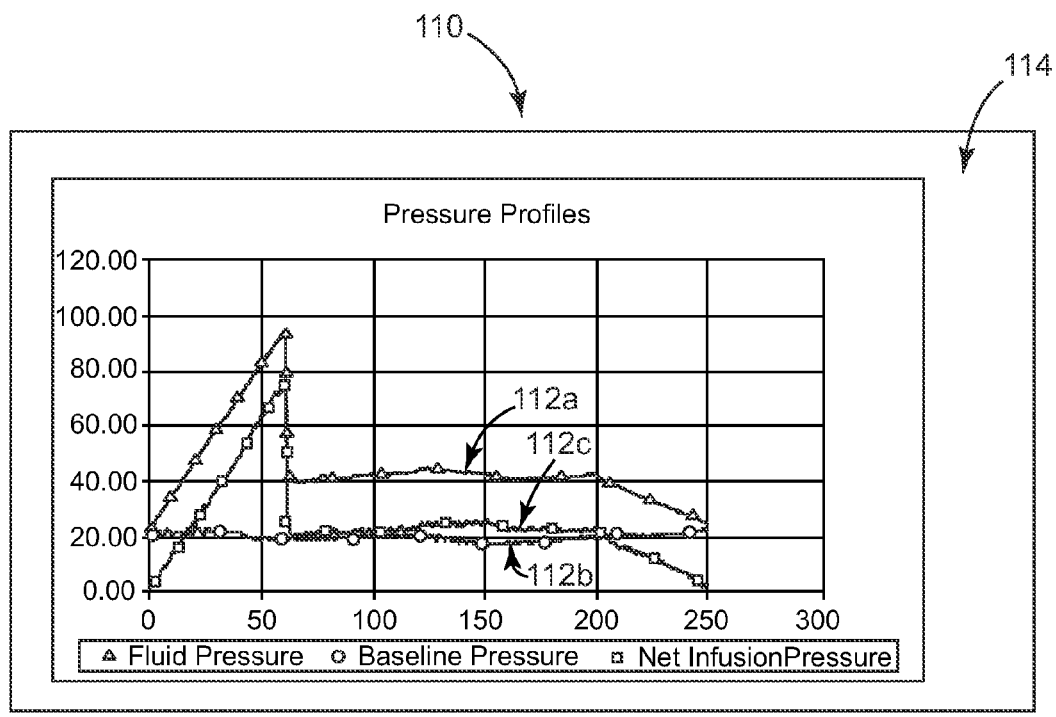

Another display 110 otherwise indicative of leakage is provided in FIG. 4B, and includes a measured pressure profile 112a, a baseline pressure profile 112b, and a net infusion pressure profile 112c, all displayed on a display screen 114. Pursuant to the above explanation, the display 110 can provide the user with information indicative of infusate delivery effectiveness, and in particular infusate leakage. In particular, by comparing the net infusion pressure profile 112c (or the measured pressure profile 112) with the baseline pressure profile 112b, the user is afforded the ability to conclude that leakage occurred approximately 200 minutes into the infusion monitoring procedure.

Figure 4C:
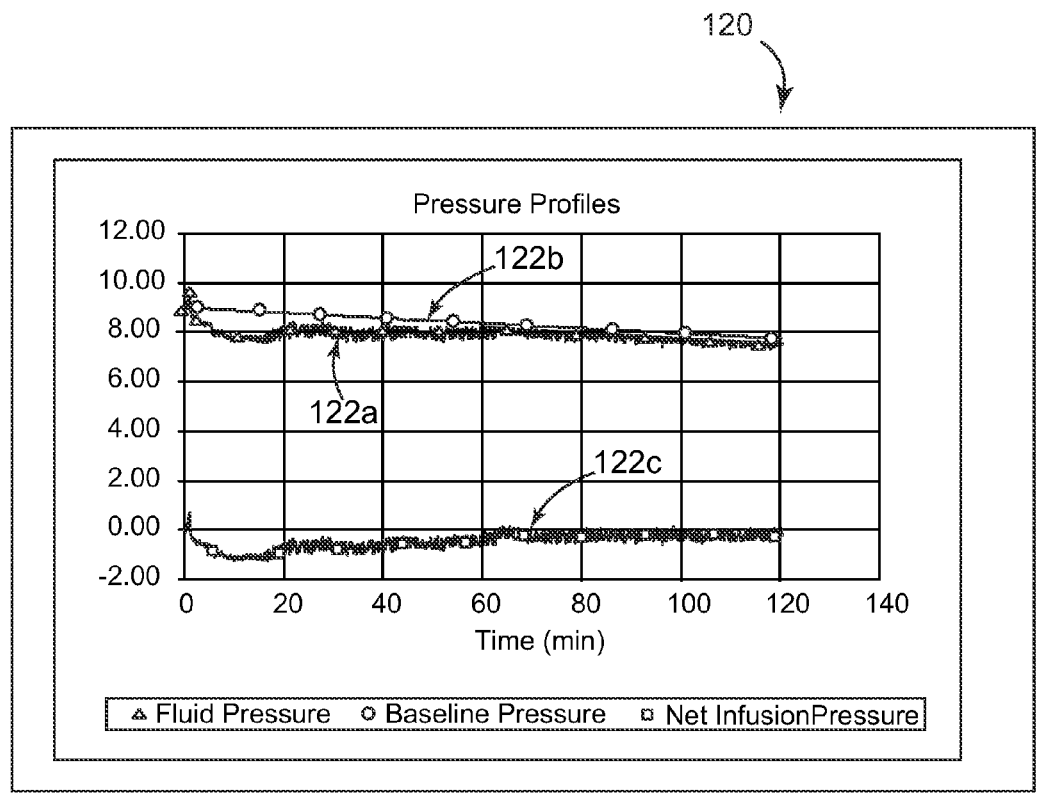

Yet another display 120 otherwise indicative of leakage is provided in FIG. 4C, and includes a measured pressure profile 122a, a baseline pressure profile 122b, and a net infusion pressure profile 122c, all displayed on a display screen 124. Based upon an evaluation of the net infusion pressure profile 122c alone, a user can conclude that leakage, in the form of immediate backflow, has occurred. No pressure peak was ever formed (e.g., the intermediate region B of FIG. 2), and the net infusion pressure profile 122c is constantly at or near zero.

Figure 4D:
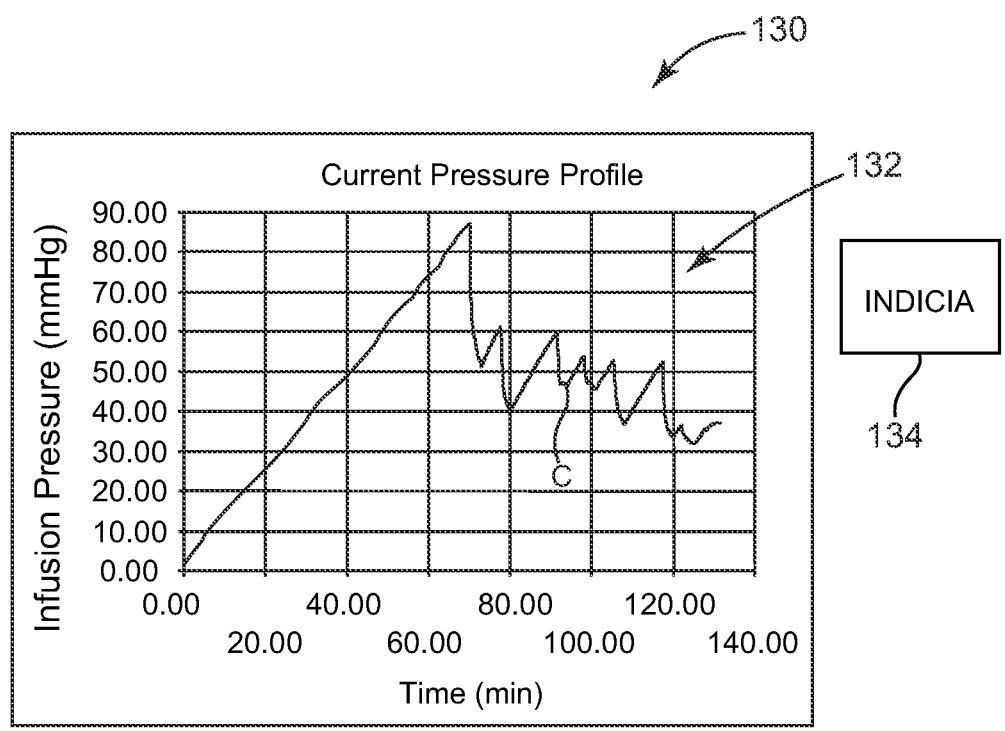

FIG. 4D illustrates yet another display 130 including a pressure profile 132 that can be interpreted by a user as being indicative of an occurrence of infusate backflow or leakage.

In particular, the steady state pressure region C of the pressure profile 132 indicates that a steady state pressure was not achieved, and an overall downward (i.e., decreasing pressure) is observed. Under these circumstances, the clinician can determine that infusate backflow has occurred.

As a point of reference, the pressure profile 132 was obtained during IPA drug infusion testing performed on an ovine brain under conditions where infusate backflow was visually observed at the catheter/tissue entry point. Thus, the ability of the system 20 (FIG. 1) to generate information indicative of infusate backflow/leakage has been confirmed. Further, had the infusion test procedure resulting in the pressure profile 132 been allowed to continue (e.g., longer than 130 minutes), it can be assumed that a steady state pressure approximating the baseline pressure of the target site (i.e., cranial pressure) would eventually have been reached. Thus, to further assist the clinician in evaluating the pressure profile 132 for an occurrence of infusate backflow, the display 130 can further include baseline indicia 134 (illustrated generally) indicative of a baseline pressure associated with the target tissue. The baseline indicia 134 is similar to the baseline indicia described above, and provides a further reference point for the clinician to evaluate for possible infusate backflow. In addition or alternatively, the indicia 134 can provide instructions to a clinician for analyzing the pressure profile 132; a report or analysis of infusate backflow independently generated by the processor 28 (FIG. 1) in analyzing the pressure profile 132; one or more reference pressure profiles; etc.

In addition to formulating and displaying one or more of the net infusion pressure profile, the measured pressure profile and/or the baseline pressure profile, in other embodiments (and returning to FIG. 1), the system 20 is adapted to display a corresponding, reference pressure profile associated with a successful IPA drug infusion for a similar infusate at a similar infusion site. The reference pressure profile can be obtained through experimentation, can be theoretical, or both. To this end, the processor 28 can be electronically connected to, or include, an electronic library provided with the memory 34 otherwise containing previously generated, reference pressure profiles for a number of different drugs and infusion sites. With this configuration, the processor 28 and/or a separate controller (not shown) is electronically connected to a user input device 60 (e.g., keyboard, stylus, mouse, etc.) through which the user can input and/or select various procedure parameters associated with the IPA drug infusion procedure to be performed (e.g., the infusate name (generic or tradename); characteristics of the infusate such as viscosity, metabolism, etc.; and/or infusion site (e.g., putamen, globus palidus, etc.); etc.). Based upon the inputted information, the processor 28 (or other system 20 component) searches the library 34 for a reference pressure profile having corresponding procedure parameter(s).

Figure 5A:
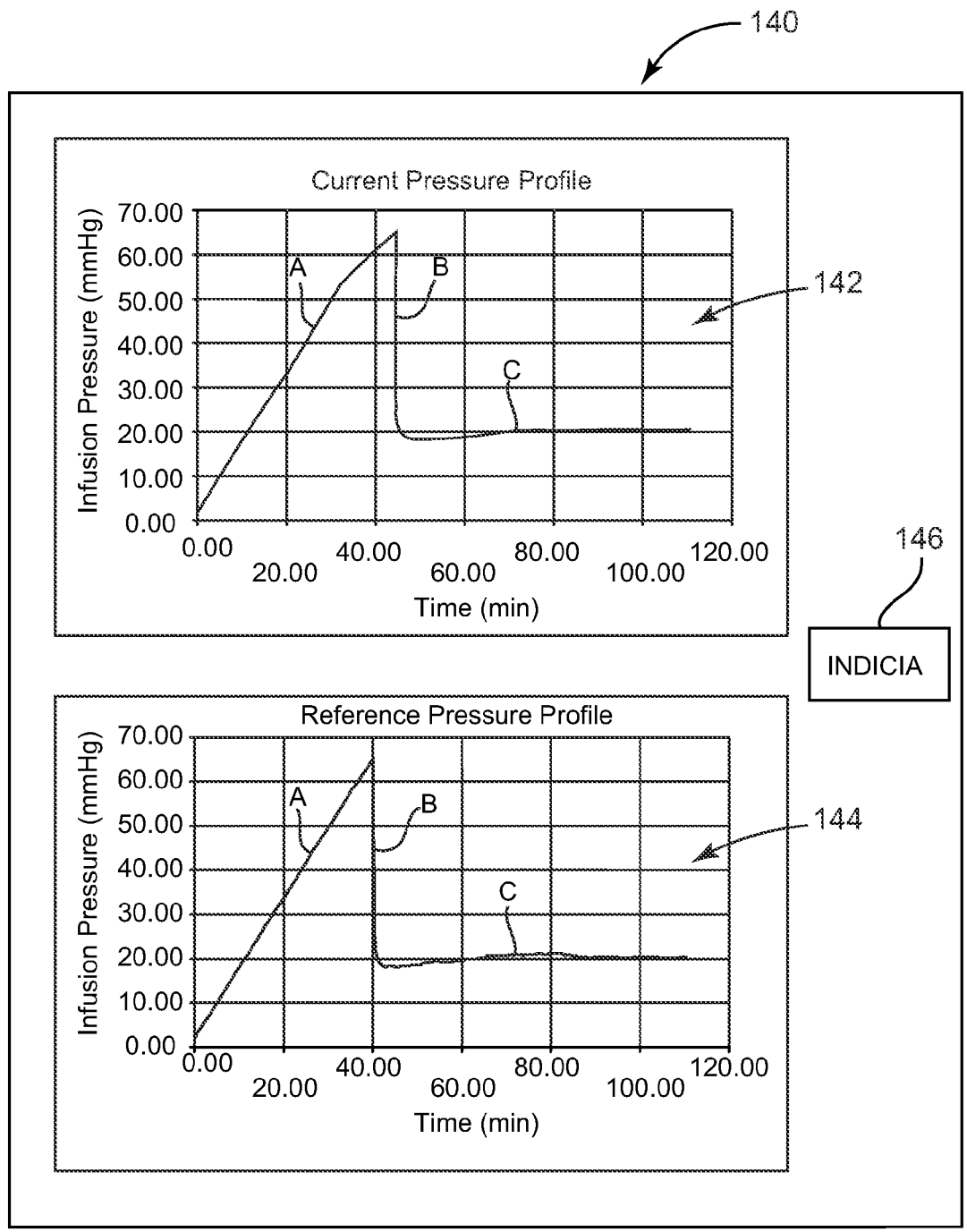
FIGS. 5A and 5B are exemplary displays generated by the system of FIG. 1, including a pressure profile.

During or following the actual or current IPA drug infusion procedure, the processor 28 is programmed to prompt display of the current pressure profile (e.g., the net infusion pressure profile) for the procedure (again, based on information signaled from the sensor 26) and the corresponding, selected reference pressure profile. One example of a display 140 indicative of whether or not the current IPA drug infusion procedure is/was successful (in terms of infusate delivery effectiveness) is shown in FIG. 5A, and includes the current pressure profile 142 and the selected reference pressure profile 144. Based upon a comparison of the current pressure profile 142 and the selected reference pressure profile 144, the user can evaluate whether the current IPA drug infusion procedure was successful in effectively delivering the infusate to the target site. For example, the user can base the evaluation on whether the current pressure profile 142 has approximately the same shape (e.g., plus or minus 10%) as the reference pressure profile 144; whether the current pressure profile 142 transitions from the initial region A to the intermediate region B and/or a transitions from the intermediate region B to the constant pressure region C at approximately the same point in time (relative to initiation of the procedure) as the reference pressure profile 144; the maximum and/or steady state pressures of the current pressure profile 142 approximate corresponding values of the reference pressure profile 144; etc.

Figure 5B:
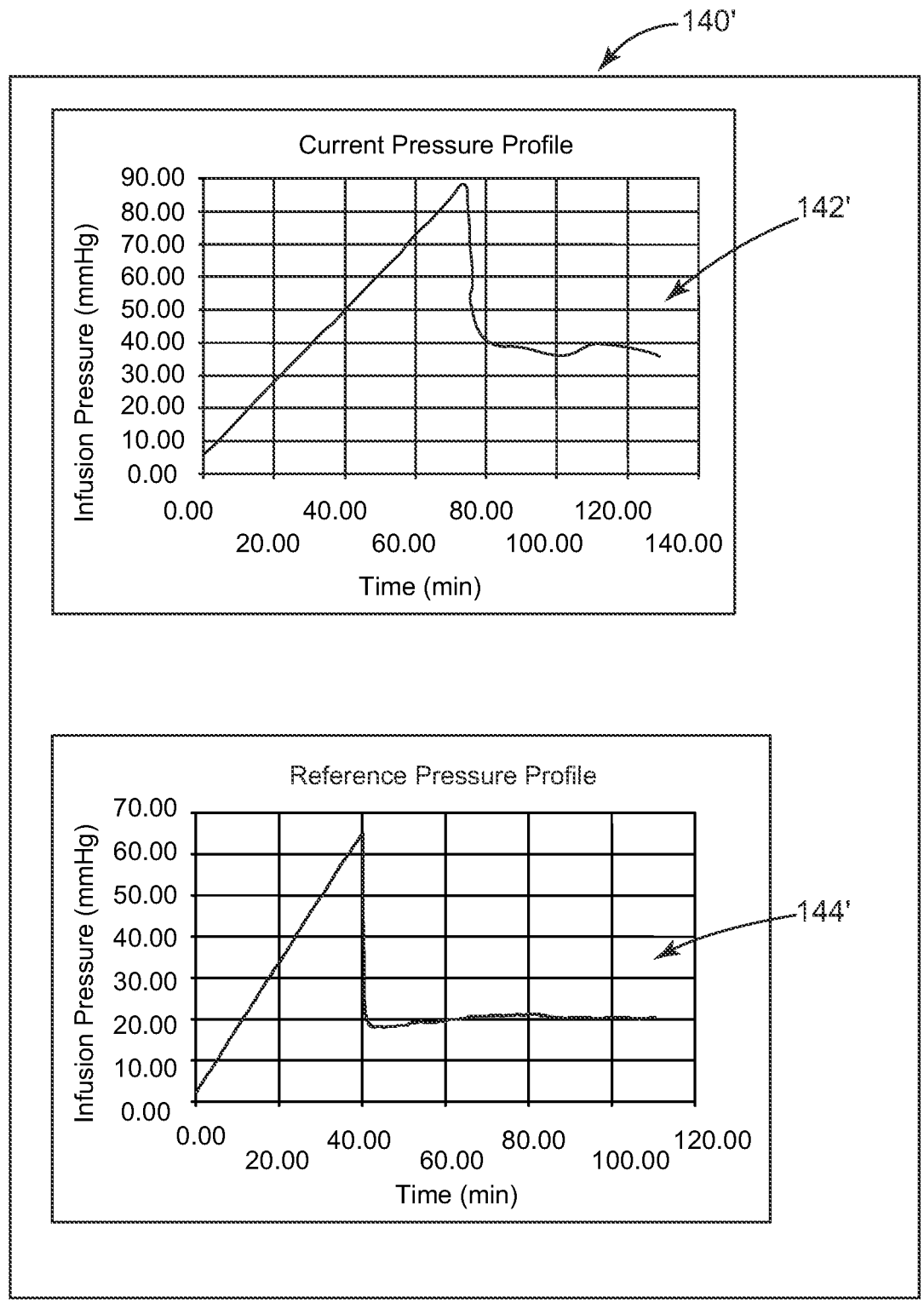

As a point of reference, the display 140 of FIG. 5A is indicative of a successful infusion (in terms of infusate delivery effectiveness) in that the current and referenced pressure profiles 142, 144 closely match one another. Conversely, a comparison of the current and reference pressure profiles 142', 144' of the alternative display 140' of FIG. 5B is indicative of an unsuccessful infusion (again, in terms of infusate delivery effectiveness).

Returning to FIG. 5A, in addition to the current and reference pressure profiles 142, 144, the display 140 can optionally include indicia 146 (illustrated generally) that informs the user of one or more of the procedure parameter(s) associated with the selected reference pressure profile 144 (so the user can confirm that an appropriate reference pressure profile is being displayed); general instructions to assist the clinician in comparing the current and reference pressure profiles 142, 144 as part of the infusate delivery effectiveness evaluation; results of an automated analysis/comparison of the current and reference pressure profiles 142, 144 performed by the processor 28 (FIG. 1); etc.

In addition, or as an alternative, to displaying information indicative of a success of the current IPA drug infusion procedure, in other embodiments the processor 28 (FIG. 1) is programmed to provide information indicative of the type of tissue that is being/was infused (with infused tissue type being another infusate delivery effectiveness criteria). As a point of reference, for certain IPA infusion procedures, the infusate exit port 32 (FIG. 1) of the delivery tube 24 (FIG. 1) may need to be delivered through differing tissue types having differing permeability characteristics and/or "blindly" maintained within a first tissue type that is adjacent a second tissue type. An intracerebral application is one example; in particular, for IPA infusion procedures performed on the patient's brain, the target site tissue can be at or within grey matter (e.g., putamen), or at or within white matter (e.g., corona radiata). It is believed that with constant flow IPA intracerebral drug infusions, the steady state pressure is different (e.g., lower) for white matter as compared to grey matter (e.g., white matter is more permeable than grey matter). Other parenchymal infusions may present similar target site characteristics.

Figure 6A:
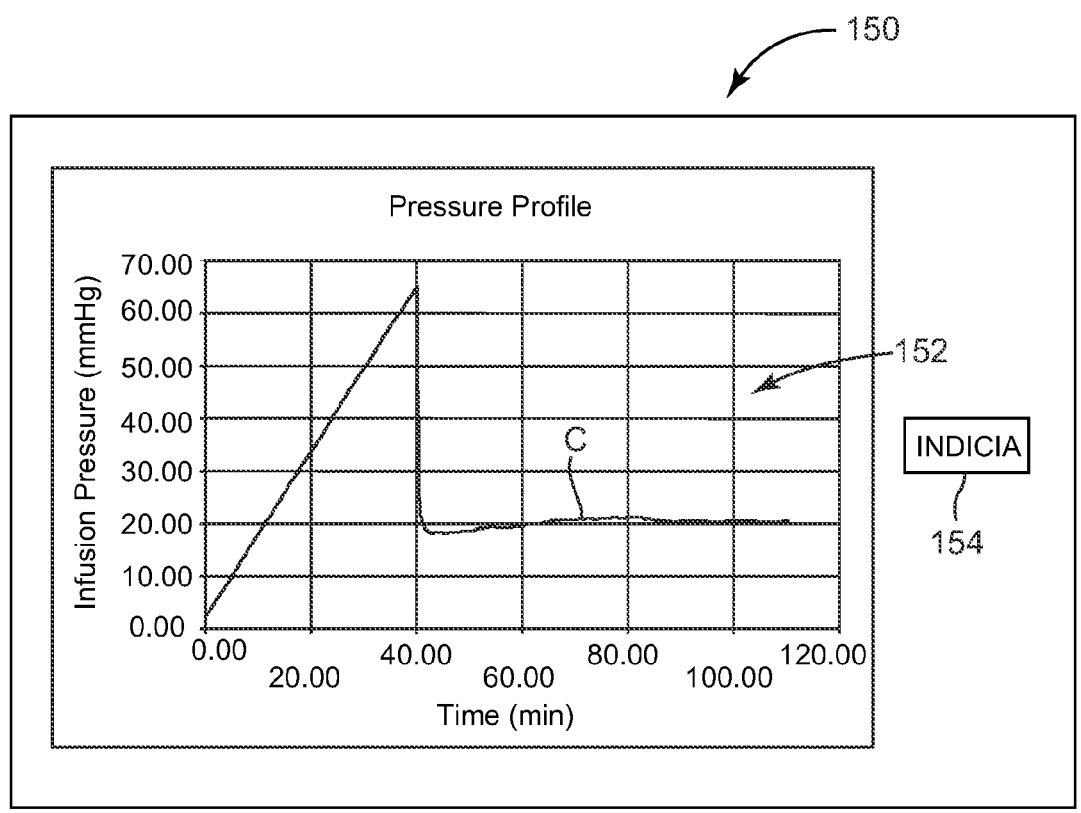
FIGS. 6A and 6B are exemplary displays generated by the system of FIG. 1, including an exemplary pressure profile indicative of infused tissue type.
Figure 6B:
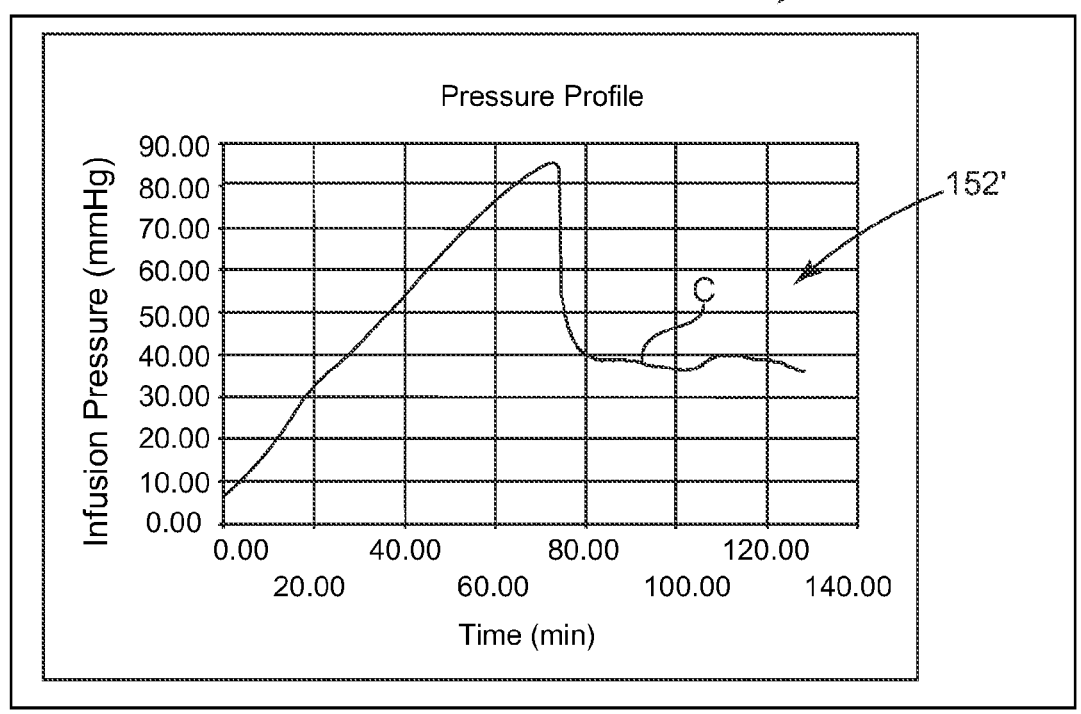

The system 20 can incorporate the above discoveries in providing a user with information indicative of the type of tissue into which the drug is being/was infused. For example, in some embodiments, the processor 28 is adapted to generate a pressure profile (e.g., a net infusion pressure profile) associated with the current IPA procedure as described above, and prompt display of the generated pressure profile to the user for evaluation of infused tissue type. One example of a display 150 indicative of infused tissue type is provided in FIG. 6A and includes a pressure profile 152 generated for an IPA drug infusion procedure performed in white matter of a brain. The pressure profile 152 is characterized by a steady state pressure region C having an average pressure of approximately 20 mmHg. FIG. 6B illustrates a display 150' including a pressure profile 152' generated for an IPA drug infusion procedure performed in grey matter of a brain, and is characterized by a steady state pressure region C having an average pressure of approximately 40 mmHg.

A user intending to perform an IPA drug infusion procedure on brain white matter, upon reviewing the display 150, and in particular the pressure profile 152, can conclude that the infusate was delivered to white matter tissue upon confirming that the steady state pressure region C exhibits a steady state pressure close (plus or minus 10%) to expected. To assist in this comparison, the display 150 can optionally further include indicia 154 (illustrated generally) that conveys information to the user relevant to this evaluation such as expected steady state pressure value for the tissue in question. Even further, the display 150 can include a reference pressure profile (not shown) generated as described above, for example by referring to a library of reference pressure profiles and selecting a reference pressure profile generated using or assuming procedural condition(s) corresponding with the procedural condition(s) actually employed with the current IPA drug infusion procedure. While the infused tissue type information has been described with specific reference to brain or intracerebral medical applications, similar information can be generated for IPA drug infusion procedures performed at other anatomical locations.

In addition to the above, other infusate delivery effectiveness characteristics or criteria may further be implicated by the system 20. In some embodiments, a pressure profile (e.g., net infusion pressure profile) for the current IPA drug infusion procedure, a reference pressure profile, and baseline indicia are simultaneously displayed such that the user is afforded the ability to evaluate multiple aspects of an infusion procedure without the requirement of separate visualization equipment (e.g., MR imaging). Notably, the infusate delivery effectiveness information can be generated and displayed for both acute and chronic IPA drug infusion applications. For acute infusion applications, the information generated and displayed by the system 20 can be indicative of specific problems. For example, where the formulated pressure profile indicates a higher-than-expected peak pressure (between regions A and B in FIG. 2), a user can conclude that the infusate exit port 32 may be plugged.

Figure 7A:
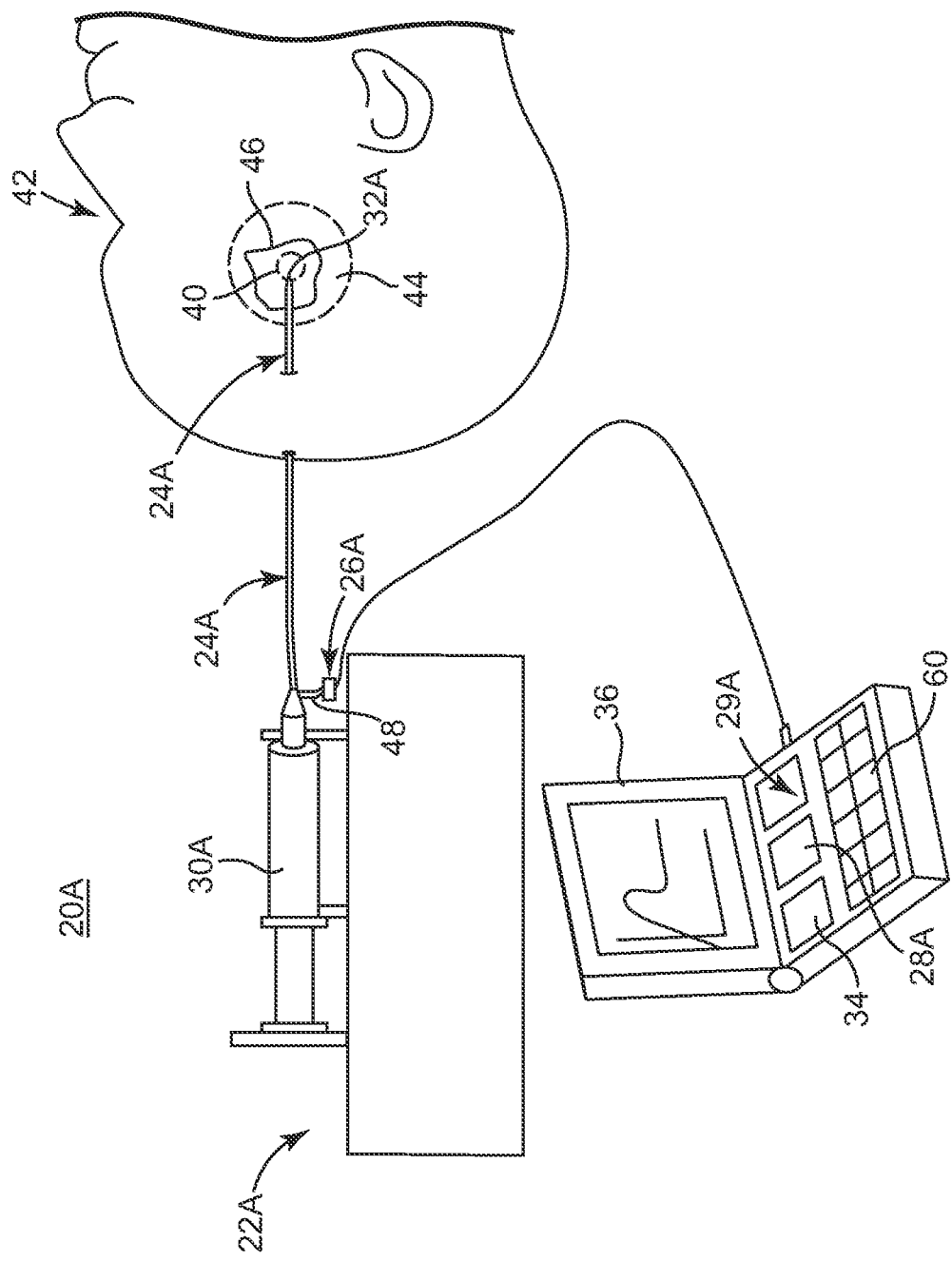
FIG. 7A is a schematic illustration, with portions in block form, of an acute IPA drug infusion system in accordance with principles of the present disclosure and showing one possible application to a human body.

With the above in mind, one embodiment of an IPA drug infusion system 20A in accordance with aspects of the present disclosure adapted for an acute infusion procedure is provided in FIG. 7A. The system 20A includes a pump device 22A, a delivery tube 24A, a sensor 26A, and a processor 28A (shown as part of a computing device 29). The pump device 22A maintains a supply or source 30A (referenced generally) of a drug (not shown), for example a therapeutic agent in liquid form, and is fluidly connected to the delivery tube 24A. The delivery tube 24A can consist of one, two, or more sections, and terminates at an infusate exit port 32A that is otherwise disposed at a parenchymal tissue target site 40 of a patient 42 where the drug or agent is to be infused. With the but one embodiment of FIG. 7A, the infusate exit port 32A is situated to infuse the drug or agent into a brain 44 of the patient 42, for example a putamen 46 of the brain 44, it being understood that a number of other parenchymal tissue sites can also be targeted. With respect to the intracerebral application reflected in FIG. 7A, the delivery tube 24A can be located at the target site 40 via an auxiliary component (not shown), such as a cannula (it being understood that the cannula is removed following delivery tube 24A insertion), and/or can have a more rigid construction.

The sensor 26A, such as a pressure transducer, is fluidly connected to a fluid pathway 48 (or "sensor pathway") for sensing information indicative of a pressure at the infusate exit port 32A. The sensor pathway 48 is shown schematically in FIG. 7A; as described below, the sensor pathway 48 can be fluidly connected with the infusate pathway (not shown) established by the delivery tube 24A (i.e., the sensor pathway is fluidly in-line with the infusate exit port 32A), or can be defined separate from the infusate pathway and terminate in close proximity to the infusate exit port 32A. Regardless, the sensor 26A is communicatively coupled to the processor 28A that otherwise acts upon sensed information signaled by the sensor 26A as described above. To this end, the system 20A can include further components (not shown) coupled between the sensor 26A and the processor 28A that assist in converting information signaled by the sensor 26A to a format useful by the processor 28A (e.g., an amplifier can be provided to augment a signal from the sensor 26A, etc.). Regardless, the pump device 22A and the processor 28A (and other related components such as the memory 34 and/or the display screen 36 where provided) are external the patient 42 during use.

Figure 7B:
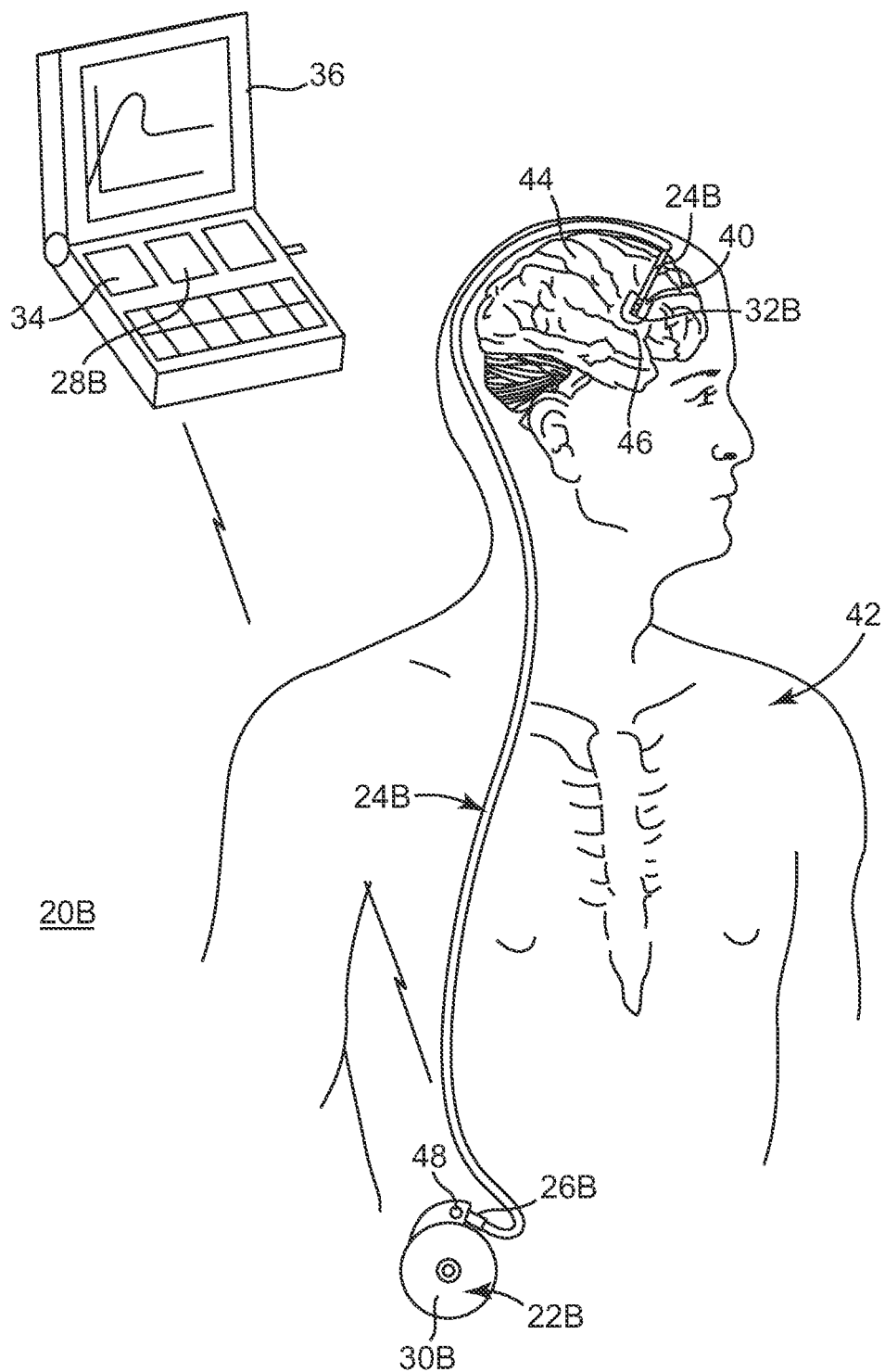
FIG. 7B is a schematic illustration, with portions in block form, of a chronic IPA drug infusion system in accordance with principles of the present disclosure and showing one possible implantation in a human body.

An alternative embodiment IPA drug infusion system 20B adapted for chronic infusion is provided in FIG. 7B. Once again, the system 20B includes a pump device 22B (referenced generally), a delivery tube 24B, a sensor 26B, and a processor 28B (shown in block form). The pump device 22B is provided as part of an implantable infusion pump device (IIP), for example a Syncromed™ IIP manufactured by Medtronic, Inc., of Minneapolis, Minn., that forms a reservoir maintaining a supply or source 30B (referenced generally) of a drug (not shown). The IIP 22B is ordinarily surgically implanted subcutaneously in the pectoral or abdominal region of the patient 42. Regardless, the delivery tube 24B is a single or multi-part catheter fluidly connected to an outlet port 48 of the IIP 22B, and thus the supply/reservoir 30B. Further, the delivery tube 24B is implanted within the patient 42 such that infusate exit port 32B thereof is disposed at the parenchymal tissue target site 40 of the patient 42 where the drug or agent is to be infused. In the medical application portrayed in FIG. 7B, the infusate exit port 32B is situated to infuse the drug or agent into the putamen 46 of the brain 44, it being understood that a number of other parenchymal tissue sites can also be targeted.

The sensor 26B, such as a pressure sensor, is fluidly connected to a fluid pathway for sensing information indicative of pressure at the infusate exit port 32B. With the one embodiment of FIG. 7B, the sensor 26B can be located at a burr hole anchor (not shown) formed by the IIP 22B, although other locations and/or configurations are equally acceptable. Regardless, the sensor 26B is communicatively coupled to the processor 28B that otherwise acts upon sensed information signaled by the sensor 26B as described above. In the one embodiment shown, the processor 28B is located external the patient 42, with the sensor 26B being telemetrically linked to the processor 28B (or to a corresponding telemetry module provided with the IIP 22B that is, in turn, communicatively connected to the sensor 26B). The external processor can further include or be electronically connected to the optional memory 34 and/or display screen 36. Alternatively, the processor 28B can be provided as part of the IIP 22B, and telemetrically linked to an external processor/controller (not shown) that otherwise includes the display screen 36 (where provided). Where necessary, the memory/library 34 can be provided as part of the IIP 22B or the external controller.

Figure 7C:
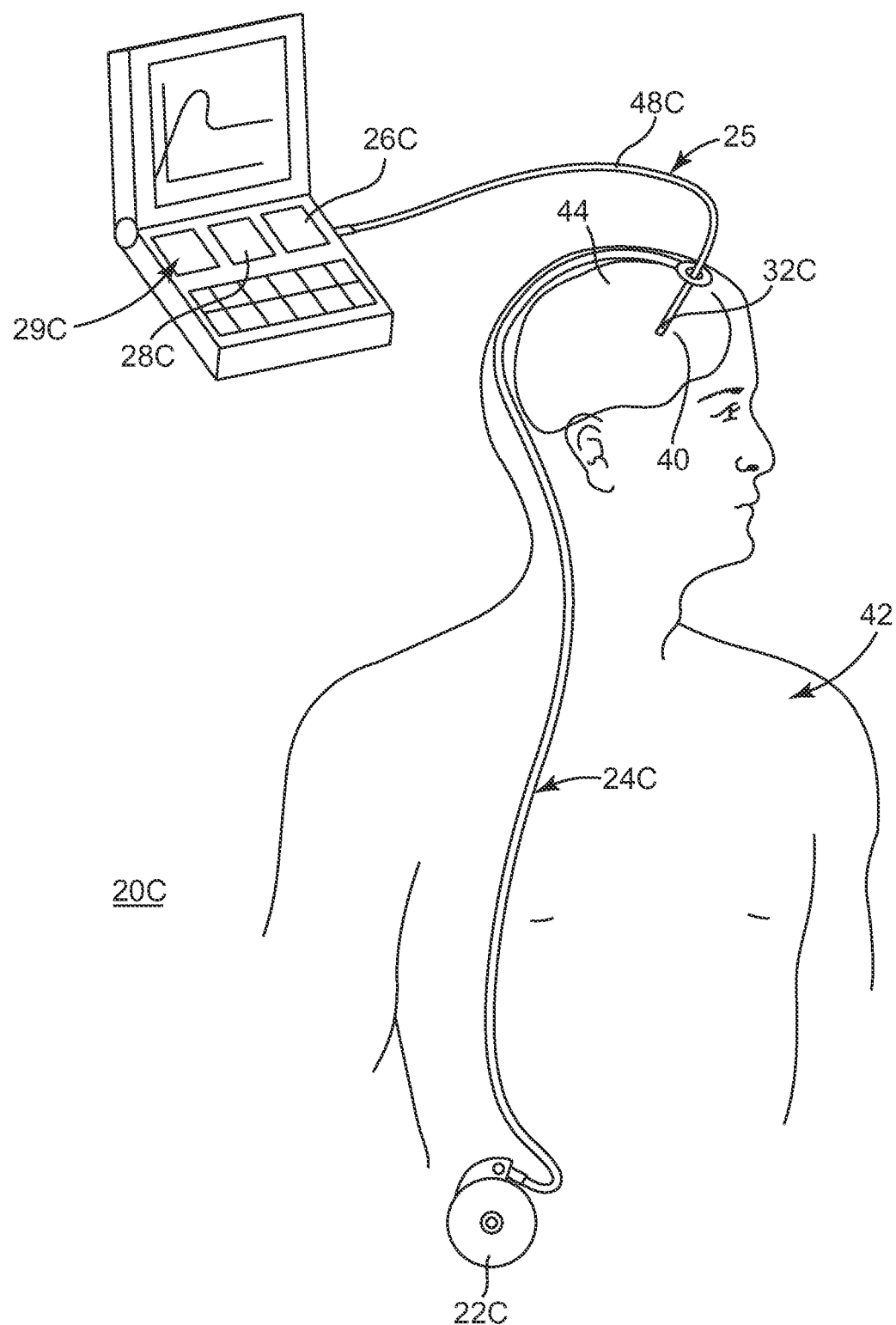
FIG. 7C is a schematic illustration, with portions in block form, of another chronic IPA drug infusion system in accordance with principles of the present disclosure and showing one possible implantation in the human body.

Another related embodiment IPA drug infusion system 20C adapted for chronic infusion is provided in FIG. 7C. The system 20C includes a pump device 22C, a delivery tube 24C, a sensor 26C, and a processor 28C (as part of an external computing device 29C). Similar to the embodiment of FIG. 7B, the pump device 22C is provided as part of an IIP. The sensor 26C is physically carried by the computing device 29C, and is fluidly connected by tubing 25 to a sensor pathway 48C (referenced generally) for sensing information indicative of pressure at the infusate exit port 32C of the delivery tube 24C (e.g., pressure in the infusate pathway). With the one embodiment of FIG. 7C, then, the sensor 26C is periodically connected to the patient 42 for performing an infusion monitoring procedure as described above, whereas the IIP 22C and the delivery tube 24C are more permanently implanted.

Figure 8A:
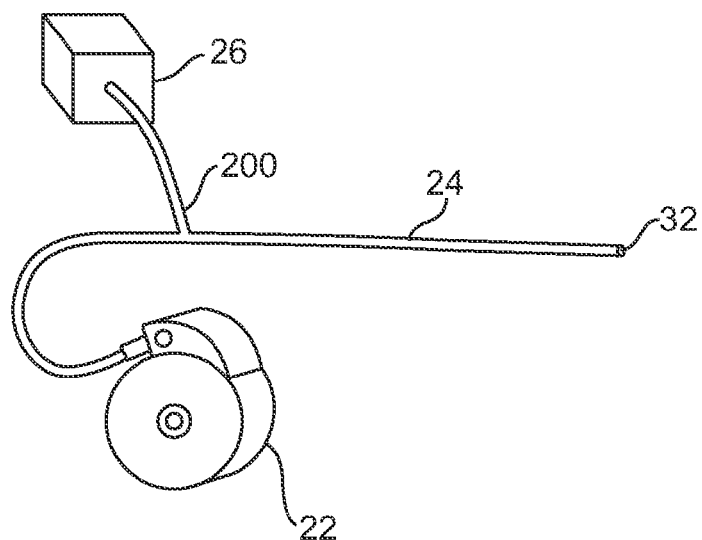
FIG. 8A is a simplified, perspective view of portions of the system of FIG. 1, including a sensor fluidly connected in-line with an infusate pathway established by a delivery tube.
Figure 8B:
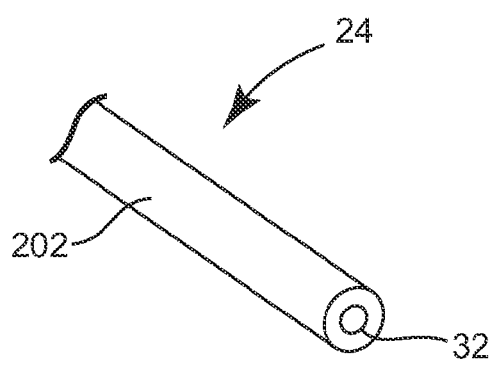
FIGS. 8B and 8C are simplified perspective views of a distal portion of the delivery tube of FIG. 8A.
Figure 8C:
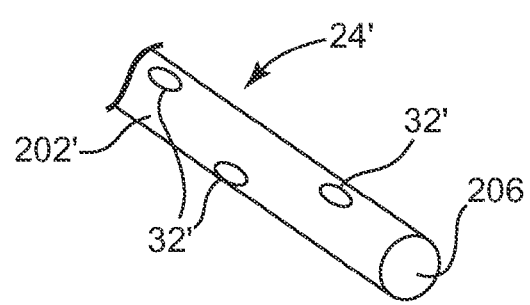

As indicated above, measuring of pressure within the delivery tube 24 (e.g., pressure in the infusate pathway) can be accomplished in a variety of fashions, and in particular relative to how the sensor 26 is fluidly associated with the delivery tube 24. For example, in one embodiment shown in FIG. 8A, the sensor 26 is, via tubing 200, fluidly connected "in-line" with the infusate pathway established by the delivery tube 24. In this regard, because the infusate (not shown) is provided as an incompressible liquid, the sensor 26 can be fluidly connected (via the tubing 200) anywhere along the infusate pathway established by the pump device 22/delivery tube 24. With this one approach, the delivery tube 24 can incorporate various constructions to establish the infusate exit port 32. For example, FIG. 8B illustrates one embodiment of the delivery tube 24 forming the infusate exit port 32 as a single opening at a distal portion 202 thereof. Alternatively, as shown in FIG. 8C, the delivery tube 24' can form one or more infusate exit ports 32' as radial holes at the distal portion 202'. With this one embodiment, a distal tip 206 of the delivery tube 24' can be closed.

Figure 9:
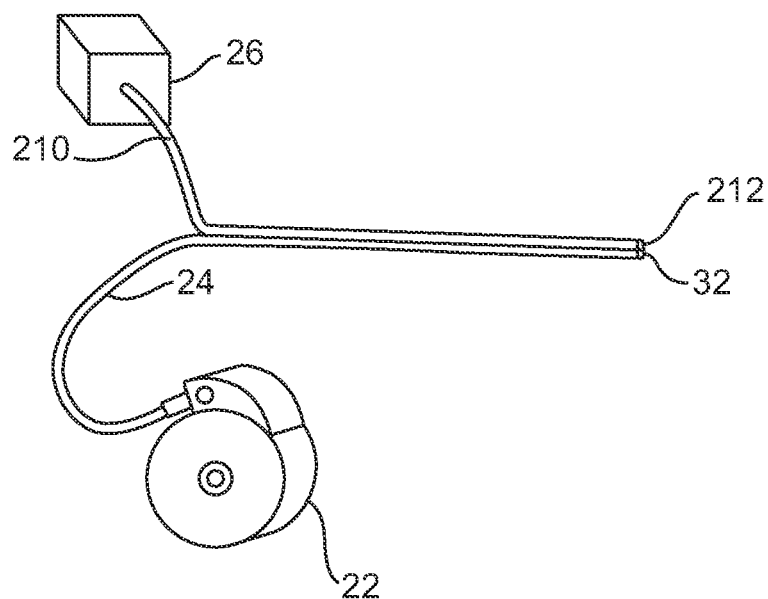
FIG. 9 is a simplified, perspective view of portions of the system of FIG. 7, including a sensor indirectly connected by a sensor pathway to an infusate pathway established by a delivery tube.

An alternative embodiment sensor/delivery tube construction is provided in FIG. 9. With this alternative approach, the sensor 26 is fluidly connected to a sensor conduit 210 (e.g., silicone tubing) that terminates at a sensor exit port 212. The conduit 210 can be associated with the delivery tube 24 in a variety of fashions as described below. Regardless, the sensor exit port 212 is in close proximity to the infusate exit port 32 such that the sensor 26 measures, via the sensor exit port 212, pressure of a volume of infusate (not shown) formed in the tissue (not shown) surrounding the infusate exit port 32. This measured pressure, in turn, represents a close approximation of the infusion pressure in the infusate pathway of the delivery tube 24.

Figures 10A, 10B:
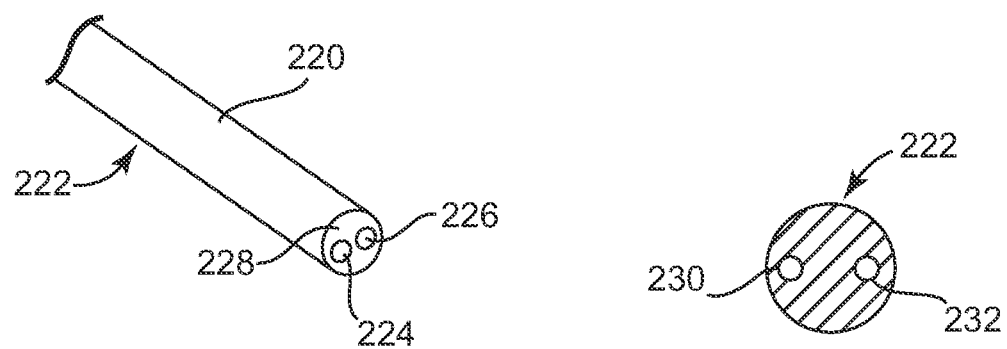
FIG. 10A is a simplified perspective view of a distal portion of the delivery tube of FIG. 9 according to some embodiments.
FIG. 10B is a cross-sectional view of the delivery tube of FIG. 10A.

In one embodiment, the sensor conduit 210 is integrally formed by or with the delivery tube 24. For example, FIGS. 10A and 10B illustrate a distal portion 220 of a multi-lumen delivery tube 222. An infusate exit port 224 and a sensor exit port 226 are formed at a distal tip 228 of the tube 222. The infusate exit port 224 is fluidly connected via a lumen (or infusate pathway) 230 (FIG. 10B) to the pump device 22 (FIG. 9). Conversely, the sensor exit port 226 is fluidly connected to the sensor 26 (FIG. 9) via a lumen (or sensor pathway) 232 (FIG. 10B) and additional branching conduit (not shown, but akin to the conduit 210 of FIG. 9).

Figure 11A:
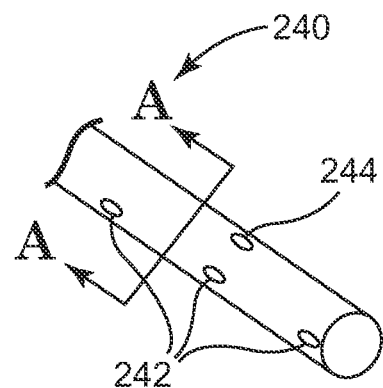
FIG. 11A is a simplified, perspective view of a distal portion of the delivery tube of FIG. 9 according to some embodiments.
Figure 11B:
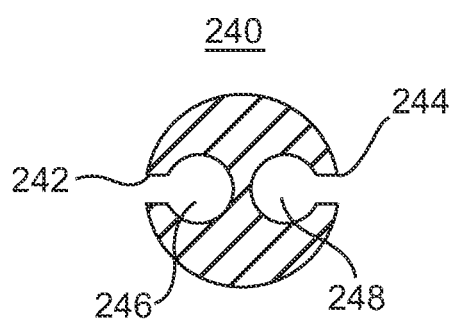
FIG. 11B is a cross-sectional view of the delivery tube of FIG. 11A.
Figure 11C:
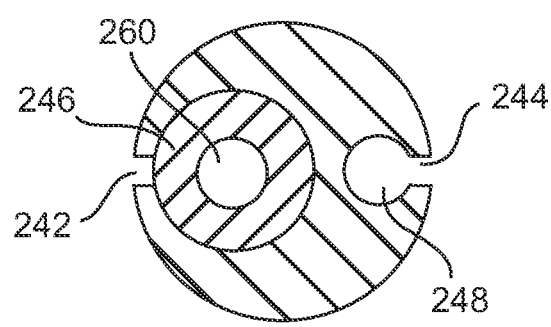
FIG. 11C is a cross-sectional view of the delivery tube of FIG. 11A illustrating an alternative embodiment in accordance with principles of the present disclosure.

Alternatively, as shown in FIG. 11A, a multi-lumen delivery tube 240 can be provided having one or more infusate exit ports 242 and a single sensor exit port 244. In one embodiment reflected in FIG. 11B, respective ones of the infusate exit ports 242 are fluidly connected to a lumen or infusate pathway 246 that in turn is fluidly connected to the pump device 26 (FIG. 9). The sensor exit port 244 is fluidly connected to a lumen or sensor pathway 248 that establishes a fluid connection to the sensor 26 (FIG. 9). In yet another embodiment, and with reference to FIG. 11C, a permeable membrane 260 can be disposed within the infusate pathway/lumen 246.

The IPA drug infusion systems and methods of the present disclosure provide a marked improvement over previous designs and techniques. The user is provided valuable feedback information from which an infusate delivery effectiveness of a particular IPA drug infusion procedure can be evaluated without requiring visualization equipment that is either highly expensive, or for many IPA drugs, simply not available.

Although the present disclosure has been described with reference to preferred embodiments, workers skilled in the art will recognize that changes can be made in form and detail without departing from the spirit and scope of the present disclosure. For example, while the IPA drug infusion system has been described as a standalone implementation, in other embodiments, an existing IPA drug infusion system can be modified or retrofitted in accordance with aspects of the present disclosure. For example, an existing IPA drug infusion system that otherwise includes a controller or similar processor can be modified to add a pressure sensor and software capable of programming the processor to generate a pressure profile. In other embodiments, a plurality of delivery tubes can be provided along with a corresponding number of sensors; the resultant IPA drug infusion system is adapted to generate and display information indicative of infusate delivery effectiveness for each of the delivery tubes, such as a net infusion pressure profile associated with each delivery tube. In the event one or more of the formulated pressure profiles (e.g., net infusion pressure profiles) are indicative of leaking or backflow, the user can then decide to return to surgery to reposition the delivery tube(s) in question.

What is claimed is:

1. A system for use with an intraparenchymal drug infusion procedure in which a drug is delivered from a source to an intracerebral target site via an infusate pathway, the system comprising:
    a sensor positioned to sense a parameter indicative of pressure in the infusate pathway;
    a display device; and
    a processor programmed to:
        generate a pressure profile for a current intraparenchymal drug infusion procedure infusing drug through the infusate pathway to the intracerebral target site based upon information from the sensor,
        generate comparative information relating to the current intraparenchymal drug infusion procedure,
        prompt the display device to simultaneously display the pressure profile and the comparative information, the simultaneous display being indicative of infusate delivery effectiveness of the current intraparenchymal drug infusion procedure, including indicative of whether a therapeutically effective volume of distribution of the infusate remains at the intracerebral target site.

2. The system of claim 1, further comprising a conduit fluidly forming a sensor pathway that connects the sensor to the infusate pathway.

3. The system of claim 2, wherein the conduit branches from a delivery tube otherwise defining the infusate pathway such that the sensor pathway is fluidly in-line with the infusate pathway.

4. The system of claim 1, further comprising a conduit fluidly connected to the sensor and terminating in a sensor exit port, wherein the sensor exit port is located in close proximity to an exit port of the infusate pathway.

5. The system of claim 4, wherein the conduit is connected to a delivery tube otherwise defining the infusate pathway.

6. The system of claim 1, wherein the processor is programmed to generate the pressure profile on a real-time basis.

7. The system of claim 1, wherein the pressure profile is a pressure-time curve.

8. The system of claim 1, wherein the processor is programmed to prompt the display device to display the pressure profile in graph form.

9. The system of claim 1, wherein the processor is programmed to determine baseline pressure information of an intended target site of the current intraparenchymal drug infusion procedure, the comparative information including the baseline pressure information.

10. The system of claim 9, wherein the baseline pressure information is based upon information from the sensor, and is a sum of an interstitial fluid pressure and a hydrostatic pressure difference between a height of the sensor and a height of the infusate exit port.

11. The system of claim 9, wherein the processor is programmed to determine baseline pressure information on a real-time basis.

12. The system of claim 9, wherein the processor is further programmed to formulate a net infusion pressure profile as a function of fluid pressure, as indicated by the sensor, and the baseline pressure information.

13. The system of claim 1, wherein the system further includes a memory storing a library of reference pressure profiles in graphical form.

14. The system of claim 13, wherein the processor is further programmed to select a reference pressure profile from the library, the comparative information including the selected reference pressure profile.

15. The system of claim 14, wherein the processor is programmed to prompt the display device to simultaneously display the pressure profile and the selected reference pressure profile.

16. The system of claim 14, wherein the processor is programmed to select the reference pressure profile from the library based upon user-entered information relating to a type of the drug being delivered with the current intraparenchymal drug infusion procedure and an intended infusion site of the current intraparenchymal drug infusion procedure.

17. The system of claim 16, wherein the user-entered information relating to an intended infusion site includes a designation of white matter or gray matter.

18. The system of claim 1, wherein the pressure profile is indicative of infused tissue type.

19. The system of claim 1, wherein the pressure profile is indicative of infusate leakage.

20. The system of claim 1, further comprising:
- a pump device for delivering the drug from a source located outside of the patient; and
- a delivery tube fluidly coupled to the pump for delivering drug from the pump to an infusate exit port of the tube;
- wherein the pump and the tube combine to define an infusate pathway to the infusate exit port.

21. The system of claim 20, wherein the pump device is adapted to produce a constant flow of the pumped drug.

22. The system of claim 20, wherein the system is adapted to perform an intracerebral drug infusion procedure.

* * * * *